United States Patent
Zhang

(10) Patent No.: US 9,868,735 B2
(45) Date of Patent: Jan. 16, 2018

(54) BENZAZEPINE KETONE COMPOUNDS AS GLYCOGEN PHOSPHORYLASE INHIBITOR, PREPARATION METHOD THEREFOR, AND MEDICAL USES

(71) Applicant: CHENGDE MEDICAL UNIVERSITY, Chengde, Hebei (CN)

(72) Inventor: Liying Zhang, Hebei (CN)

(73) Assignee: CHENGDE MEDICAL UNIVERSITY, Chengde, Hebei (CN)

( * ) Notice: Subject to any disclaimer, the term of this patent is extended or adjusted under 35 U.S.C. 154(b) by 41 days.

(21) Appl. No.: 15/022,581

(22) PCT Filed: Sep. 23, 2014

(86) PCT No.: PCT/CN2014/000861
§ 371 (c)(1),
(2) Date: Mar. 17, 2016

(87) PCT Pub. No.: WO2015/043111
PCT Pub. Date: Apr. 2, 2015

(65) Prior Publication Data
US 2016/0229848 A1    Aug. 11, 2016

(30) Foreign Application Priority Data
Sep. 30, 2013 (CN) .......................... 2013 1 0453330

(51) Int. Cl.
| | | |
|---|---|---|
| C07D 471/04 | (2006.01) | |
| A61K 31/553 | (2006.01) | |
| A61K 31/554 | (2006.01) | |
| C07D 413/12 | (2006.01) | |
| C07D 417/12 | (2006.01) | |

(52) U.S. Cl.
CPC .......... *C07D 471/04* (2013.01); *A61K 31/553* (2013.01); *A61K 31/554* (2013.01); *C07D 413/12* (2013.01); *C07D 417/12* (2013.01)

(58) Field of Classification Search
CPC .. A61K 31/553; A61K 31/554; C07D 413/12; C07D 417/12; C07D 471/04
See application file for complete search history.

(56) References Cited

U.S. PATENT DOCUMENTS

| | | |
|---|---|---|
| 6,107,329 A | 8/2000 | Hoover et al. |
| 6,297,269 B1 | 10/2001 | Hulin et al. |
| 2004/0002495 A1 | 1/2004 | Sher et al. |

FOREIGN PATENT DOCUMENTS

| | | |
|---|---|---|
| EP | 0832066 B1 | 9/2001 |
| WO | 03/074513 A2 | 9/2003 |
| WO | 2005/085194 A2 | 9/2005 |
| WO | 2006/059163 A1 | 6/2006 |
| WO | 2006/059164 A2 | 6/2006 |

OTHER PUBLICATIONS

W. Ross Tracey et al., "Cardioprotective effects of ingliforib, a novel glycogen phosphorylase inhibitor" Am J Physiol Heart Circ Physiol, vol. 286, 2004, pp. H1177-H1184.
Carole Sourbier et al., "The Phosphoinositide 3-Kinase/Akt Pathway: A New Target in Human Renal Cell Carcinoma Therapy" Cancer Res, vol. 66, No. 10, May 15, 2006, pp. 5130-5142.
Hong-Bin Sun, "Drug discovery based on pharmacological interference with glycometabolism" Journal of China Pharmaceutical University, 2006, vol. 37, No. 1, pp. 1-8.
Nikos G. Oikonomakos, "Glycogen Phosphorylase as a Molecular Target for Type 2 Diabetes Therapy" Current Protein and Peptide Science, 2002, 3, pp. 561-586.
Richard D Connell, "Glucagon Antagonists for the Treatment of Type 2 Diabetes" Expert Opinion on Therapeutic Patents, 1999, vol. 9, No. 6, pp. 701-709.
Ana Martinez et al., "Glycogen Synthase Kinase 3 (GSK-3) Inhibitors as New Promising Drugs for Diabetes, Neurodegeneration, Cancer, and Inflammation" Medicinal Research Reviews, vol. 22, No. 4, 373-384, 2002.

*Primary Examiner* — Sreeni Padmanabhan
*Assistant Examiner* — Jody Karol
(74) *Attorney, Agent, or Firm* — Novick, Kim & Lee, PLLC; Allen Xue

(57) ABSTRACT

The present invention relates to the field of pharmaceutical chemistry, and particularly to a novel class of benzazepine ketone derivatives (I), their preparation method and their pharmaceutical uses. The compounds have glycogen phosphorylase inhibiting effect and can be used in the preparation of anti-diabetes and its complications medicaments, anti-cerebral ischemia medicaments, anti-cardiovascular diseases medicaments, blood lipid-lowering medicaments, weight-reducing medicaments, anti-atherosclerosis medicaments, medicaments for treating metabolic syndrome or anti-tumor medicaments. The present invention also relates to a preparation method of the class of compounds and pharmaceutical formulations containing the same.

11 Claims, 1 Drawing Sheet

BENZAZEPINE KETONE COMPOUNDS AS GLYCOGEN PHOSPHORYLASE INHIBITOR, PREPARATION METHOD THEREFOR, AND MEDICAL USES

TECHNICAL FIELD

The present invention relates to the field of pharmaceutical chemistry and particularly relates to a novel class of benzazepine ketone glycogen phosphorylase inhibitors. The compounds can be used in the preparation of anti-diabetes and its complications medicaments, anti-cerebral ischemia medicaments, anti-cardiovascular diseases medicaments, blood lipid-lowering medicaments, weight-reducing medicaments, anti-atherosclerosis medicaments, medicaments for treating metabolic syndrome or anti-tumor medicaments. The present invention also relates to a preparation method of the compounds and pharmaceutical compositions containing the same.

BACKGROUND ART

Glycogen metabolism is an important part of glucose metabolism. In particular, glycogen metabolic disorders become a major pathological factor in certain disease states. Research shows that the regulation and control of insulin on liver glycogen metabolism is one of the key mechanisms for maintaining whole body blood glucose equilibrium, myocardial ischemia injury has definite correlations with abnormal cardiac glycogen metabolism, and abnormal brain glycogen metabolism also has some correlations with cerebral ischemic injury (*Journal of China Pharmaceutical University*, 2006, 37, 1).

At present, some signal conducting molecules and receptor proteins of glycogen metabolism, such as glycogen synthase kinase-3, glycogen phosphorylase, protein kinase B and glucagon receptor, etc., have become potential drug targets for treating type 2 diabetes, ischemic cardiovascular diseases, tumors, psoriasis and so on (*Med. Res. Rev*, 2002, 22, 373; *Curr. Protein Pep. Sci.*, 2002, 3, 561; *Cancer Res.*, 2006, 66, 5130; *Expert Opinion Therap. Pat.*, 1999, 9, 701).

Among them, glycogen phosphorylase (GP) is a key enzyme in glycogen metabolism. Said enzyme can catalyze the phosphorolysis of glycogen to release glucose-1-phosphate, which is then converted into glucose-6-phosphate under the catalyzation of phosphoglucomutase. Glucose-6-phosphate is either converted into glucose for body tissues under the catalyzation of glucose-6-phosphatase, or directly involved in energy supply in anaerobic and aerobic metabolic pathways. Since the glycogen phosphorylase is a key factor in glycogen metabolism, the pharmacological inhibition of the glycogen phosphorylase might be used to treat the diseases associated with excessive glycogen degradation such as diabetes, ischemic myocardial injury, tumors and so on (*Curr. Protein Pept. Sci.*, 2002, 3, 561; *Am. J. Physiol. Heart. Girc. Physiol.*, 2004, 286, H177).

Moreover, hypertension and its associated pathological changes, such as atherosclerosis, hyperlipidemia and hypercholesterolemia, etc., have been all associated with elevated insulin levels. Inhibition of glycogen phosphorylase can effectively reduce insulin levels, and thus can be used in the treatment of diseases such as hypercholesterolemia, hyperinsulinemia, hyperlipidemia, atherosclerosis and myocardial ischemia, etc.

In recent years, the development of novel glycogen phosphorylase inhibitors has attracted wide attention. For example, U.S. Pat. No. 6,297,269 and European Patent Application No. EP0832066 described substituted N-(indole-2-carbonyl) amides and their derivatives as glycogen phosphorylase inhibitors. U.S. Pat. No. 6,107,329 described substituted N-(indole-2-carbonyl) glycinamides and their derivatives as glycogen phosphorylase inhibitors. European Patent Application No. WO2006059163 described pyrrolo-pyridine-2-carboxylic acid amide derivatives as glycogen phosphorylase inhibitors.

CONTENTS OF THE INVENTION

The present invention discloses for the first time benzazepine ketone compounds of Formula (I) with medicinal value, their preparation methods and pharmaceutical uses, including the use in the preparation of anti-diabetes and its complications medicaments, anti-cerebral ischemia medicaments, anti-cardiovascular diseases medicaments, blood lipid-lowering medicaments, weight-reducing medicaments, anti-atherosclerosis medicaments, medicaments for treating metabolic syndrome and anti-tumor medicaments. In particular, the compounds of Formula (I) are novel glycogen phosphorylase inhibitors and therefore can be used for treating the diseases associated with abnormal glycogen metabolism. These diseases include diabetes (particularly type 2 diabetes) and its complications, ischemic cardio-cerebrovascular diseases (particularly myocardial infarction, angina, arrhythmias, coronary artery disease, stroke, cerebral infarction or ischemic neurodegenerative diseases, etc.), hyperinsulinemia, insulin resistance, metabolic syndrome, obesity, fasting hyperglycemia and tumors. Furthermore, the present invention further provides a pharmaceutical formulation containing the compounds of Formula (I).

The present invention herein relates to the compounds of Formula (I) and pharmaceutically acceptable salts or esters thereof:

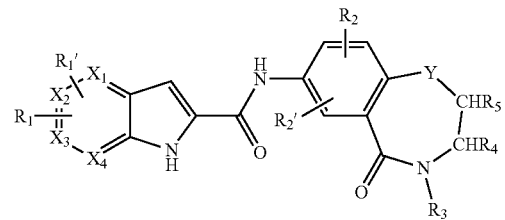

wherein, all of $X_1$, $X_2$, $X_3$ and $X_4$ are C, or one of $X_1$, $X_2$, $X_3$ and $X_4$ is N and all the others are C;

each of $R_1$ and $R_1'$, independently, is H, halogen, hydroxy, cyano, $C_{0-4}$ alkyl, $C_{1-4}$ alkoxy, fluoromethyl, difluoromethyl, trifluoromethyl, ethenyl or ethynyl;

each of $R_2$ and $R_2'$, independently, is H, halogen, hydroxy, cyano, $C_{0-4}$ alkyl, $C_{1-4}$ alkoxy, fluoromethyl, difluoromethyl, trifluoromethyl, ethenyl or ethynyl;

$R_3$ is H, unsubstituted or X-substituted linear or branched $C_{1-20}$ alkyl, alkenyl and alkynyl, substituted or X-substituted aryl, substituted or X-substituted heteroaryl;

each of $R_4$ and $R_5$, independently, is H, unsubstituted or X-substituted linear or branched $C_{1-20}$ alkyl, alkenyl or alkynyl;

Y is $CHR_6$, NH, O, S;

$R_6$ is H, unsubstituted or X-substituted linear or branched $C_{1-20}$ alkyl, alkenyl, alkynyl, phenyl, benzyl, naphthyl or nitrile group;

X represents H, F, Cl, Br, I, CN, $NO_2$, $NH_2$, $CF_3$, SH, OH, $OCH_3$, $OC_2H_5$, COOH, linear or branched $C_{1-10}$ alkyl, alkenyl, alkynyl, aryl or heteroaryl.

The preferred compounds of the above-mentioned compounds are:

all of $X_1$, $X_2$, $X_3$ and $X_4$ are C;

each of $R_1$ and $R_1'$, independently, is H, halogen, cyano;

each of $R_2$ and $R_2'$, independently, is H;

$R_3$ is H, unsubstituted or X-substituted linear or branched $C_{1-2}$ alkyl, substituted or X-substituted aryl, substituted or X-substituted heteroaryl;

each of $R_4$ and $R_5$, independently, is H;

Y is $CH_2$, NH, O;

X represents H, F, Cl, Br, I, CN, $NO_2$, $NH_2$, $CF_3$, SH, OH, $OCH_3$, $OC_2H_5$, COOH, linear or branched $C_{1-10}$ alkyl, alkenyl, alkynyl, aryl or heteroaryl.

The more preferred compounds are:

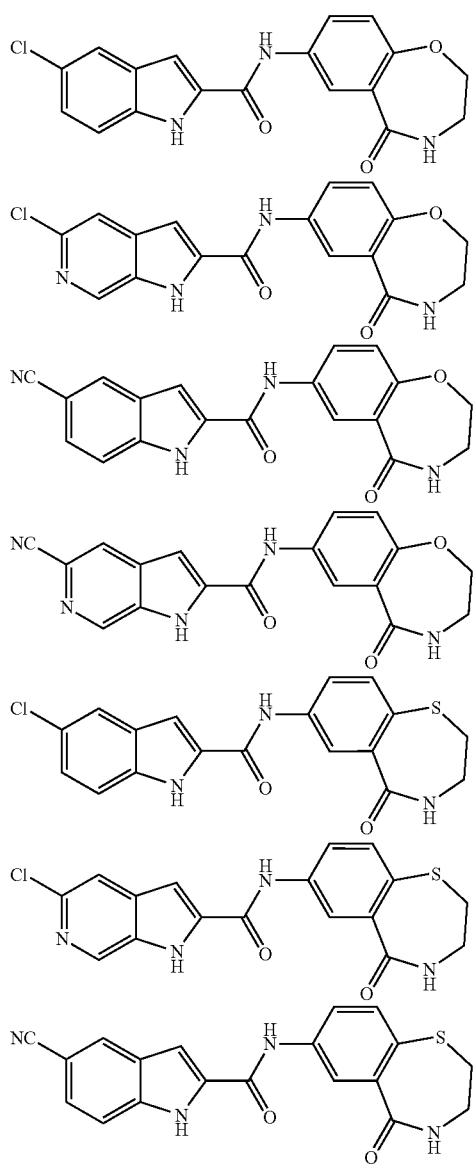

-continued

The compounds of the present invention can be prepared using the reported methods or the following method:

Substituted indole carboxylic acid or pyrrolopyridine-2-carboxylic acid and a benzazepine ketone compound are dissolved in an organic solvent, and a condensing agent, and an organic amine or an inorganic base are then added. The reaction is conducted from 1 to 72 hours at a temperature ranging from 0° C. to 45° C. The solvent is generally selected from inert solvents, particularly aprotic solvents such as acetonitrile, chloroform, dichloromethane, 1,2-dichloroethane, N,N-dimethylformamide, toluene, n-hexane, cyclohexane, tetrahydrofuran, tert-butyl methyl ether or mixed solvent of the above solvents, preferably dichloromethane, 1,2-dichloroethane or N,N-dimethylformamide. The condensing agent can be a common condensing agent for amidation, such as 1-ethyl-3-(3-dimethylaminopropyl)carbodiimide hydrochloride (EDCI), N,N'-dicyclohexylcarbodiimide (DCC), O-benzotriazolyl-N,N,N',N'-tetramethyluronium tetrafluoroborate (TBTU), 2-(7-azabenzotriazolyl)-N,N,N',N'-tetramethyluronium hexafluorophosphate (HATU), 1-propylphosphonic anhydride ($T_3P$). The inorganic base can be selected from sodium carbonate, sodium bicarbonate, potassium carbonate or potassium bicarbonate, and the organic base can be selected from N,N-diisopropylethylamine or triethylamine.

The present invention also provides pharmaceutical formulations, which comprise the compounds of Formula (I), pharmaceutically acceptable salts or esters thereof as an active agent, or pharmaceutically acceptable carriers.

Said pharmaceutically acceptable carriers are common pharmaceutical carriers in pharmaceutical field, referring to one or more inert, non-toxic, solid or liquid fillers, diluents, or adjuvants, etc., which could not act adversely with active compounds or patients.

The dosage forms of the pharmaceutical compositions according to the present invention can be tablets, capsules, pills, suppositories, soft capsules, oral liquids, suspensions, injections and other dosage forms commonly used in pharmaceutics.

Tablets and capsules for oral administration may contain conventional excipients such as fillers, diluents, lubricants, dispersants and binders.

Various dosage forms of the pharmaceutical compositions according to the present invention can be prepared according to processes well-known in pharmaceutical field.

The dose of the above active agents will be variable depending on formulations.

In general, it has been proved that the following advantageous dose can be administrated to achieve desired results: the total dose of the compounds of Formula (1) is about 0.01 to 800 mg, preferably 0.1 to 100 mg/kg per kilogram of body weight per 24 hours. If necessary, the compounds can be administrated in the form of several single doses. If necessary, however, the above dose can also be deviated, depending on type and body weight of a subject to be treated, individual behavior towards medicament, nature and severity of disease, type of formulation and administration, and time and frequency of administration.

DESCRIPTION OF FIGURES

The present invention will be further illustrated herein below with reference to examples and the figures of the accompanying drawings.

In FIG. 1 and FIG. 2, $X_1$, $X_2$, $X_3$, $X_4$, $R_1$, $R_1'$, $R_2$, $R_2'$, $R_3$, $R_4$, $R_5$, $R_6$, X and Y are as defined in the above-mentioned Formula (I).

EMBODIMENTS

Figure 1:
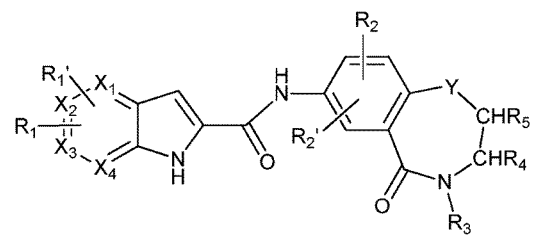
FIG. 1 indicates general formula of compounds of the present invention.
Figure 2:
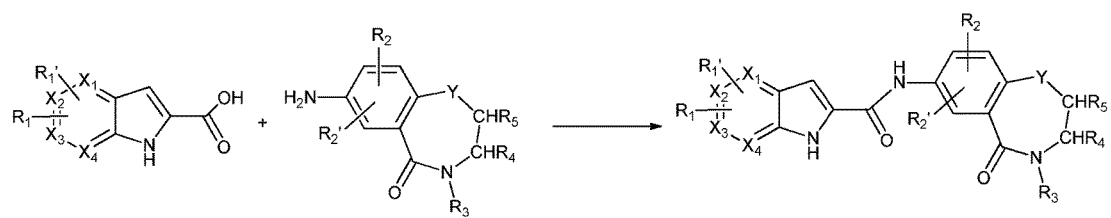
FIG. 2 indicates a preparation process of some derivatives of the present invention.

Hereinafter, the present invention will be specifically illustrated with reference to the specific examples. In the present invention, the following examples are intended to better illustrate the present invention, rather than to constitute a limitation of the protection scope of the present invention.

The implementation of the present invention will be further illustrated by way of the following examples.

Example 1

7-(5-Chloro-1H-indole-2-carboxamido)-3,4-dihydrobenzo[f][1,4]oxazepin-5(2H)-one

5-Chloro-1H-indole-2-carboxylic acid (593 mg, 3.03 mmol) and 7-amino-3,4-dihydrobenzo[f][1,4]oxazepin-5 (2H)-one (450 mg, 2.53 mmol) were dissolved in dry dichloromethane (10.0 ml), slowly added with the solution of 1-propylphosphonic acid cyclic anhydride in ethyl acetate ($T_3P$, 50 wt. %, 3.02 mL, 10.12 mmol) and N,N-diisopropylethylamine (DIPEA, 1.3 mL, 7.59 mmol). After the addition, the mixture was stirred at room temperature for 2 h under nitrogen. After completion of the reaction, the mixture was washed successively with 1N aqueous hydrochloric acid, saturated aqueous $NaHCO_3$ and saturated salt water, dried over anhydrous sodium sulfate, filtered and concentrated. The residue was separated by a reversed-phase HPLC (mobile phase: (ACN—$H_2O$ (0.1% TFA), gradient: 40% to 70%) to afford a white solid (70 mg, 16%).

ESI-MS m/z: 354.1 [M-H]$^-$.

$^1$H-NMR ($d_6$-DMSO, 400 MHz): 11.94 (s, 1H), 10.39 (s, 1H), 8.37 (t, J=4.4 Hz, 1H), 8.13 (d, J=2.0 Hz, 1H), 7.97 (dd, J=2.4, 8.8 Hz, 1H), 7.94 (dd, J=2.4, 8.8 Hz, 1H), 7.78 (s, 1H), 7.48 (d, J=8.8 Hz, 1H), 7.43 (s, 1H), 7.23 (d, J=8.4 Hz, 1H), 7.05 (d, J=8.8 Hz, 1H), 4.28 (t, J=4.4 Hz, 2H), 3.33-3.35 (m, 2H).

Glycogen Phosphorylase In Vitro Inhibitory Activity Assay

Preparation of reagents: 1) preparation of color developing solution: 5 g of ammonium molybdate was weighed, dissolved in 500 ml of 1M HCl and stirred with a stirrer until completely dissolved. Then the mixture was added with 190 mg of malachite green with stirring until completely dissolved. The solution prepared was wrapped with an aluminum foil to protect it from exposure to light; 2) preparation of buffer: ①̂ 0.5958 g of Hepes was precisely weighed and dissolved in 5 ml $H_2O$. The solution was adjusted to pH 7.2 using 10M NaOH to formulate a Hepes solution with a final concentration of 0.5 M; ②̂ 0.3728 g of KCl was precisely weighed and dissolved in 5 ml of $H_2O$ to formulate a KCl solution with a final concentration of 1 M; ③̂ 0.0255 g of $MgCl_2$ was precisely weighed and dissolved in 1 ml $H_2O$ to formulate a $MgCl_2$ solution with a final concentration of 125 mM; ④̂ 0.0476 g of EGTA was precisely weighed and dissolved in 5 ml $H_2O$. The solution was adjusted to pH 7.0 using 10M NaOH to formulate a EGTA solution with a final concentration of 25 mM; ⑤̂ 0.0152 g of G-1-P was precisely weighed and dissolved in 10 ml $H_2O$ to formulate a G-1-P solution with a final concentration of 5 mM; ⑥̂ 10 mg of glycogen was precisely weighed and dissolved in 1 ml $H_2O$ to formulate a glycogen solution with a final concentration of 10 mg/ml; 3) preparation of solution of positive drug caffeine: the caffeine was dissolved in 10 ml $H_2O$ to formulate a solution of 0.5, 5, 50 and 500 μM; 4) preparation of GPa solution: 1 μl GPa was added to 100 μl of the reaction system to achieve a final concentration of 250 ng/100 μl; 5) preparation of the solution of test compound: the test compound was dissolved in DMSO to prepare a solution with a concentration of 10 mM. Appropriate amount of compound solution was added to the reaction system to achieve different final concentrations.

Determination of dose-response curve of rabbit muscle glycogen phosphorylase activity: a dose-response curve was determined by reading OD values of various concentrations of GPa solutions at 655 nm after added with a color developing solution. The amount of GPa can be 250 ng as determined from the dose-response curve.

Experimental procedure: 1) designing PC (positive control), Blank (blank control), positive drug (caffeine); 2) adding 52 μl of reaction buffer; 3) adding the test compound to a final concentration; 4) adding 1 μl of enzyme to a final concentration of 250 ng/100 μl; 5) adding 150 μl of the color developing solution; 6) reacting at 30° C. for 20 minutes; 7) colorimetry determination at a wavelength of 655 nm; 8) reading data and calculating inhibitory activity:

Inhibitory Activity=(PC−test sample)/(PC−Blank)

The result showed that the compound in Example 1 had an $IC_{50}$<0.1 μM. The pharmacological data indicated that the compounds of Formula (I) had the effect of inhibiting glycogen phosphorylase, and therefore can be used to prepare anti-diabetes medicaments, anti-cerebral ischemia medicaments, anti-cardiovascular diseases medicaments, blood lipid-lowering medicaments, weight-reducing medicaments, anti-atherosclerosis medicaments or anti-tumor medicaments.

The invention claimed is:

1. A compound of Formula (I), or a pharmaceutically acceptable salt or ester thereof:

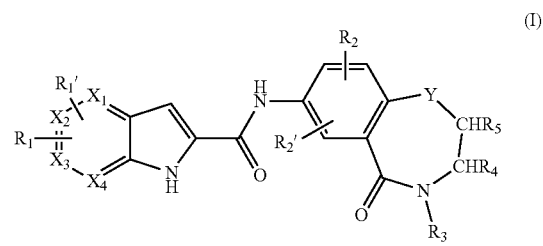

wherein,
all of $X_1$, $X_2$, $X_3$ and $X_4$ are C, or one of $X_1$, $X_2$, $X_3$ and $X_4$ is N and all the others are C;
each of $R_1$ and $R_1'$, independently, is H, halogen, hydroxy, cyano, $C_{0-4}$ alkyl, $C_{1-4}$ alkoxy, fluoromethyl, difluoromethyl, trifluoromethyl, ethenyl, or ethynyl;

each of $R_2$ and $R_2'$, independently, is H, halogen, hydroxy, cyano, $C_{0-4}$ alkyl, $C_{1-4}$ alkoxy, fluoromethyl, difluoromethyl, trifluoromethyl, ethenyl, or ethynyl;

$R_3$ is H, unsubstituted or X-substituted linear or branched $C_{1-20}$ alkyl, unsubstituted or X-substituted linear or branched $C_{1-20}$ alkenyl, unsubstituted or X-substituted linear or branched $C_{1-20}$ alkynyl, substituted or X-substituted aryl, or substituted or X-substituted heteroaryl;

each of $R_4$ and $R_5$, independently, is H, unsubstituted or X-substituted linear or branched $C_{1-20}$ alkyl, unsubstituted or X-substituted linear or branched $C_{1-20}$ alkenyl, or unsubstituted or X-substituted linear or branched $C_{1-20}$ alkynyl;

Y is $CHR_6$, NH, O, or S;

$R_6$ is H, unsubstituted or X-substituted linear or branched $C_{1-20}$ alkyl, unsubstituted or X-substituted linear or branched $C_{1-20}$ alkenyl, unsubstituted or X-substituted linear or branched $C_{1-20}$ alkynyl, phenyl, benzyl, naphthyl, or nitrile group;

X represents H, F, Cl, Br, I, CN, $NO_2$, $NH_2$, $CF_3$, SH, OH, $OCH_3$, $OC_2H_5$, COOH, linear or branched $C_{1-10}$ alkyl, linear or branched $C_{1-10}$ alkenyl, linear or branched $C_{1-10}$ alkynyl, aryl, or heteroaryl.

2. The compound of Formula (I), or the pharmaceutically acceptable salt or ester thereof according to claim 1, wherein, all of $X_1$, $X_2$, $X_3$ and $X_4$ are C;

each of $R_1$ and $R_1'$, independently, is H, halogen, or cyano;

each of $R_2$ and $R_2'$, independently, is H;

$R_3$ is H, unsubstituted or X-substituted linear or branched $C_{1-2}$ alkyl, substituted or X-substituted aryl, substituted or X-substituted heteroaryl;

each of $R_4$ and $R_5$, independently, is H;

Y is $CH_2$, NH, or O;

X represents H, F, Cl, Br, I, CN, $NO_2$, $NH_2$, $CF_3$, SH, OH, $OCH_3$, $OC_2H_5$, COOH, linear or branched $C_{1-10}$ alkyl, linear or branched $C_{1-10}$ alkenyl, linear or branched $C_{1-10}$ alkynyl, aryl, or heteroaryl.

3. The compound of Formula (I), or the pharmaceutically acceptable salt or ester thereof according to claim 1, wherein the compound is

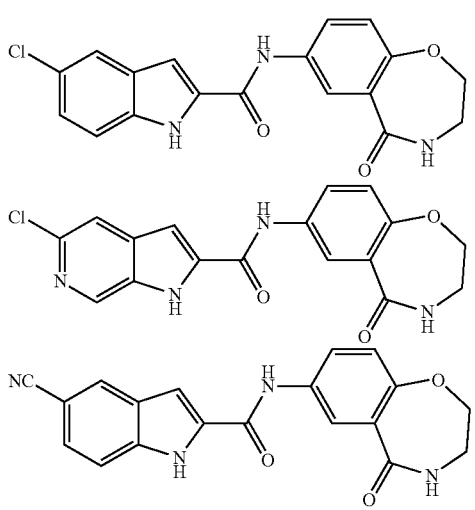

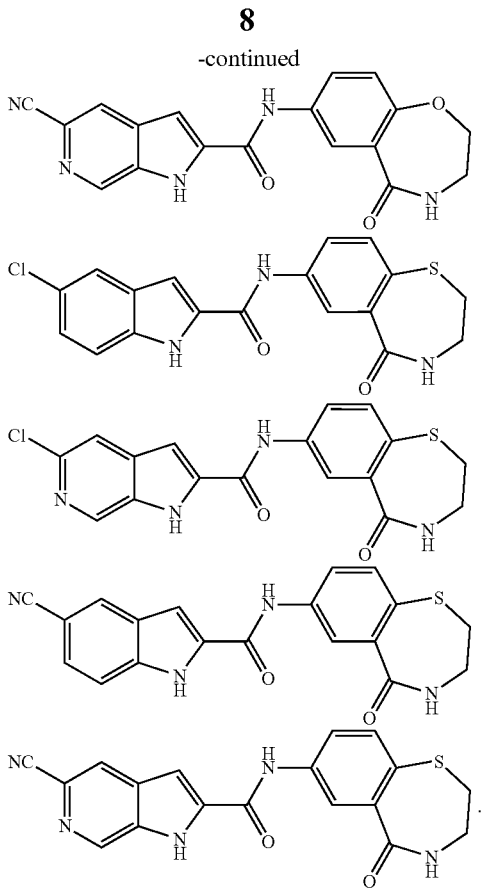

4. A method for preparing the compound of Formula (I) according to claim 1, comprising:
dissolving a substituted indole carboxylic acid or a substituted pyrrolopyridine-2-carboxylic acid, and a benzazepine ketone compound in an organic solvent to form a solution;
adding a condensing agent, and an organic amine or an inorganic base to the solution,
wherein a reaction is carried out in the solution for 1 to 72 hours at a temperature ranging from 0° C. to 45° C.

5. A pharmaceutical composition, comprising a therapeutically effective dose of the compound of Formula (I) according to claim 1, a racemic mixture thereof, an optical isomer thereof, or a pharmaceutically acceptable salt or ester thereof, and a pharmaceutically acceptable carrier.

6. The compound of Formula (I) according to claim 1, wherein the compound is a glycogen phosphorylase inhibitor.

7. The method of claim 4, wherein the solvent is selected from the group consisting of acetonitrile, chloroform, dichloromethane, 1,2-dichloroethane, N,N-dimethylformamide, toluene, n-hexane, cyclohexane, tetrahydrofuran, tert-butyl methyl ether, and mixtures thereof.

8. The method of claim 4, wherein the solvent is dichloromethane, 1,2-dichloroethane, or N,N-dimethylformamide.

9. The method of claim 4, wherein the condensing agent is selected from the group consisting of 1-ethyl-3-(3-dimethylaminopropyl)carbodiimide hydrochloride (EDCI), N,N'-dicyclohexylcarbodiimide (DCC), O-benzotriazolyl-N,N,N',N'-tetramethyluronium tetrafluoroborate (TBTU), 2-(7-azabenzotriazolyl)-N,N,N',N'-tetramethyluronium hexafluorophosphate (HATU), and 1-propylphosphonic anhydride ($T_3P$).

10. The method of claim 4, wherein the inorganic base is sodium carbonate, sodium bicarbonate, potassium carbonate, or potassium bicarbonate.

11. The method of claim 4, wherein the organic base is N,N-diisopropylethylamine or triethylamine.

* * * * *